US007011639B1

(12) United States Patent
Vigiletti

(10) Patent No.: US 7,011,639 B1
(45) Date of Patent: Mar. 14, 2006

(54) BACK MASSAGING DEVICE

(76) Inventor: Alice J. Vigiletti, 419 Grove Dr., Newton, NJ (US) 07860

( * ) Notice: Subject to any disclaimer, the term of this patent is extended or adjusted under 35 U.S.C. 154(b) by 0 days.

(21) Appl. No.: 10/782,112

(22) Filed: Feb. 19, 2004

(51) Int. Cl.
*A61F 19/00* (2006.01)

(52) U.S. Cl. ......................................... 601/136; 601/84

(58) Field of Classification Search .................. 601/84, 601/136; 18/160; 4/606
See application file for complete search history.

(56) References Cited

U.S. PATENT DOCUMENTS 1,933,989 A * 11/1933 McCollough ............... 601/136
3,279,463 A * 10/1966 Krimmel .................... 601/136
4,733,842 A * 3/1988 Wilkerson ............. 248/231.51
5,228,165 A 7/1993 Westberry et al.
D351,947 S 11/1994 Fitzgerald
5,779,653 A 7/1998 Thompson
6,089,664 A * 7/2000 Yoshida ................... 297/284.4
6,110,132 A * 8/2000 Kurpieski ................... 601/136

* cited by examiner

*Primary Examiner*—Michael Anthony Brown

(57) ABSTRACT

A the back massaging device for allowing a user to massage their back. The back massaging device includes a body member being designed for being coupled to the wall. A plurality of massaging members are coupled to the body member whereby the massaging members are designed for being positioned opposite the wall when the body member is coupled to the wall. The massaging members are designed for kneading the back of the user when the back of the user is rubbed against the body member and the massaging members.

1 Claim, 3 Drawing Sheets

BACK MASSAGING DEVICE

BACKGROUND OF THE INVENTION

1. Field of the Invention

The present invention relates to massaging devices and more particularly pertains to a new back massaging device for allowing a user to massage their back.

2. Description of the Prior Art

The use of massaging devices is known in the prior art. U.S. Pat. No. 5,228,165 describes a device for brush that is mounted to a wall and used to scrub a portion of the body of the user. Another type of massaging devices is U.S. Pat. No. 5,779,653 having an apparatus that is mounted to a wall and has multi- fingered clusters used to scrub and massage the back of the user. U.S. Pat. No. Des. 351,947 shows a back washing brush.

While these devices fulfill their respective, particular objectives and requirements, the need remains for a device that has certain improved features allowing the user to massage a greater area of the back.

SUMMARY OF THE INVENTION

The present invention meets the needs presented above by providing a body member that is mounted around a corner of a structure to allow the massaging members to forced into and around areas of the back to provide greater contact between the massaging members and the back of the user.

Still yet another object of the present invention is to provide a new back massaging device that allow the user to relax the muscles of the back while the massaging members are used to knead the back which can not be achieved with a hand held device requiring the use to flex the muscles in the upper back to position the arm in a position to allow the hand held device to be used.

Even still another object of the present invention is to provide a new back massaging device that has the massaging members in spaced relationship to allow the massaging members to conform to the shape of the back of the user.

To this end, the present invention generally comprises a body member being designed for being coupled to the wall. A plurality of massaging members are coupled to the body member whereby the massaging members are designed for being positioned opposite the wall when the body member is coupled to the wall. The massaging members are designed for kneading the back of the user when the back of the user is rubbed against the body member and the massaging members.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
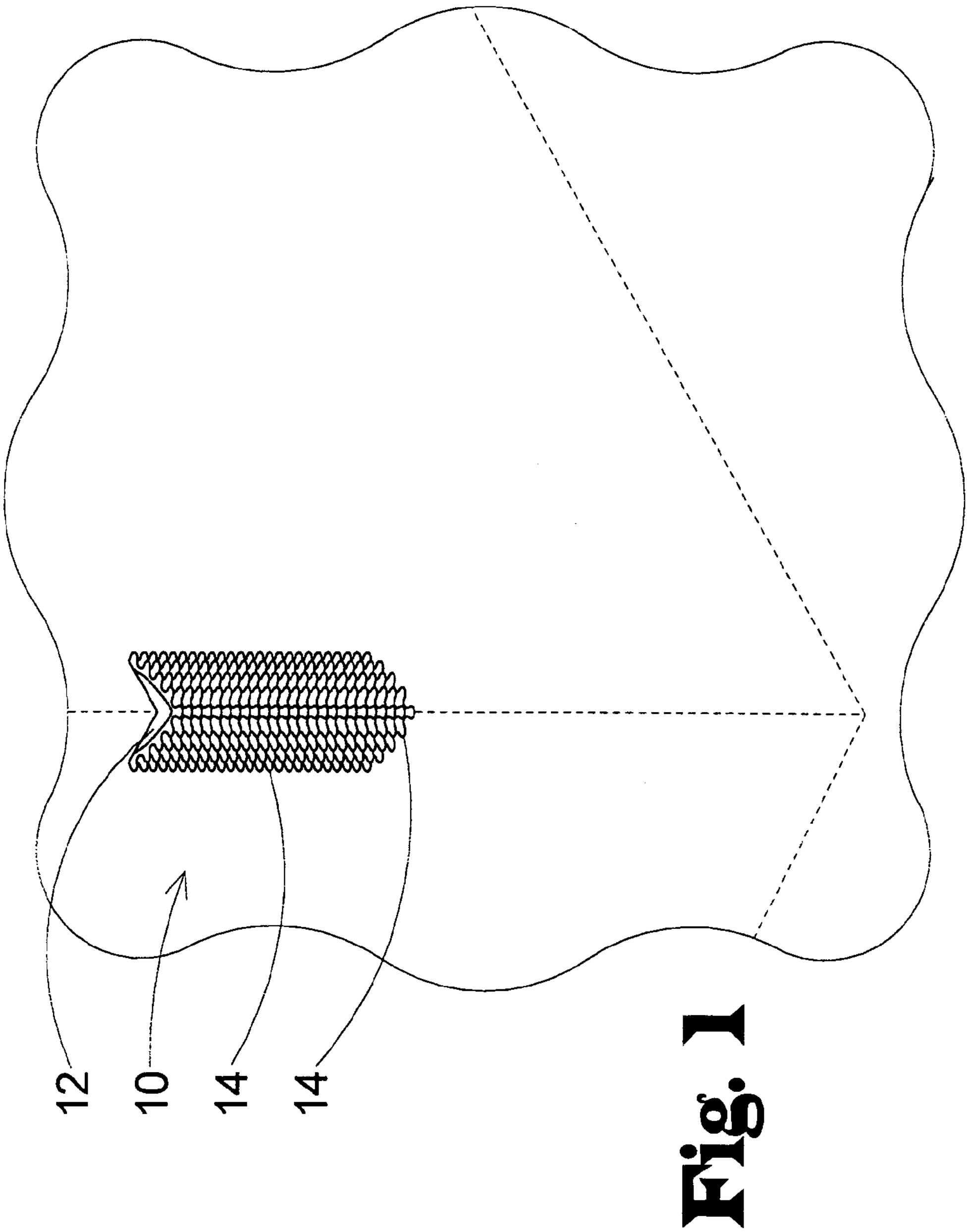
FIG. 1 is a perspective view of a new back massaging device according to the present invention shown mounted to a corner.
Figure 2:
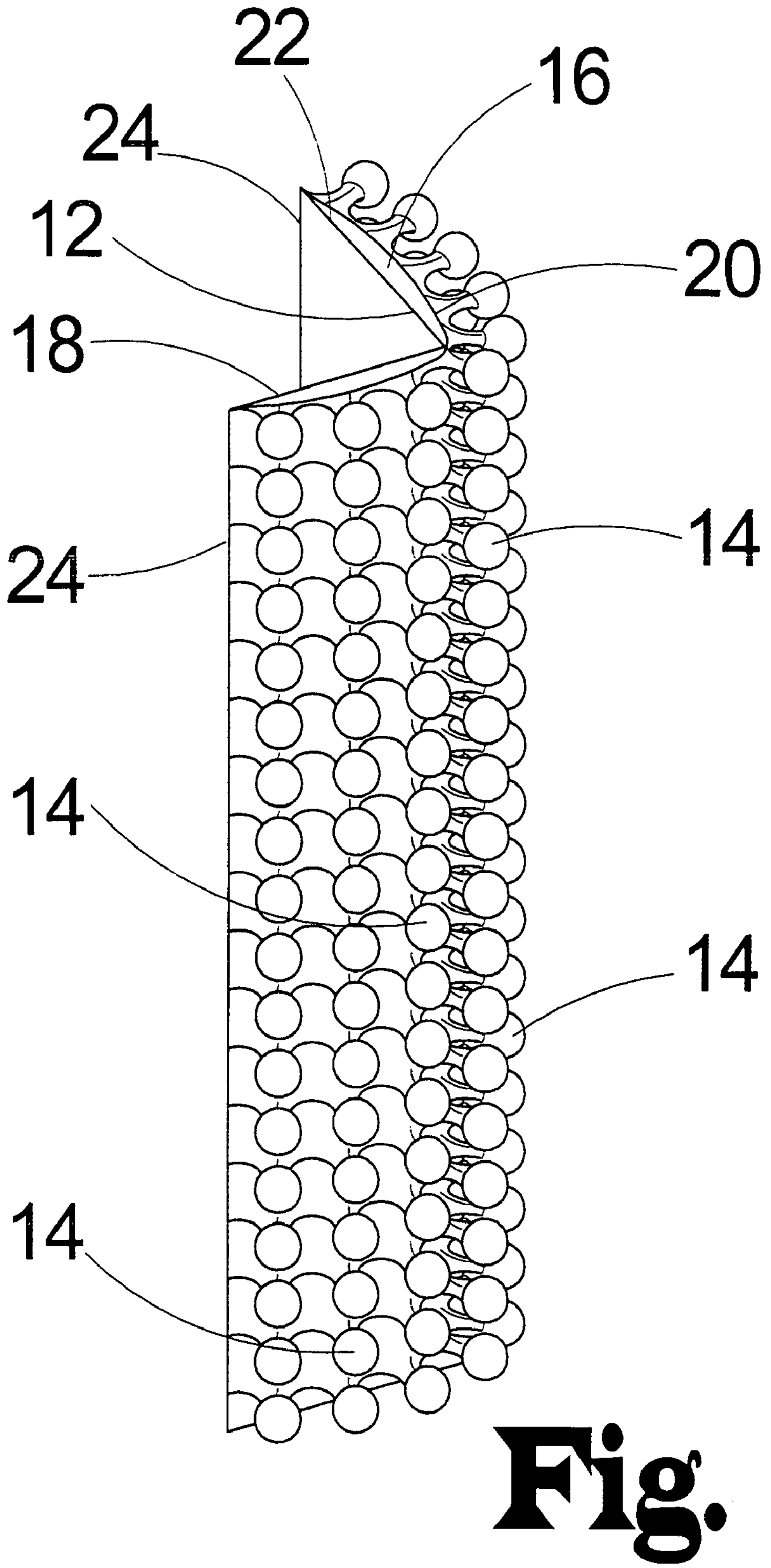
FIG. 2 is a perspective view of the present invention.
Figure 3:
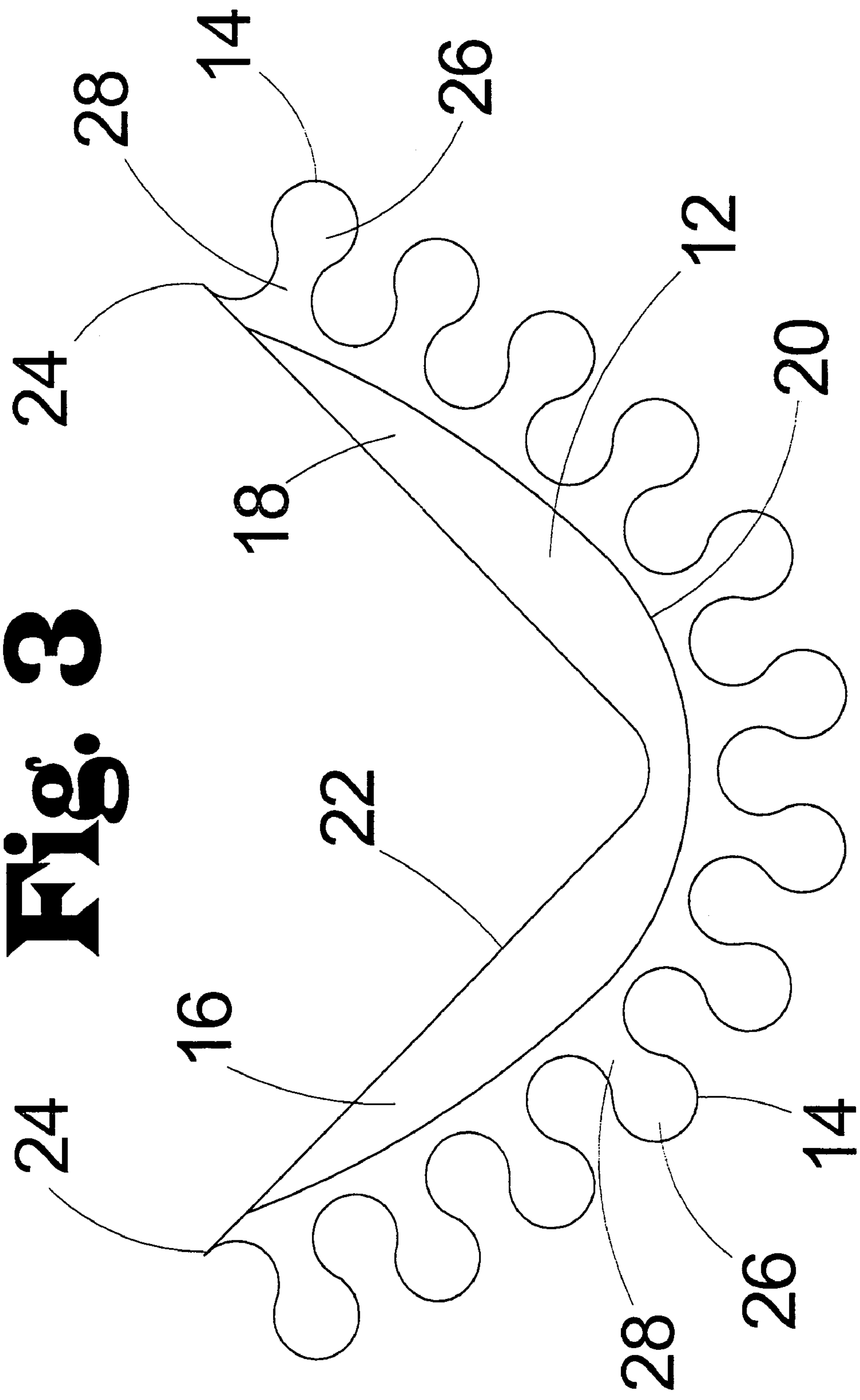
FIG. 3 is a top view of the present invention.

With reference now to the drawings, and in particular to FIGS. 1 through 3 thereof, a new back massaging device embodying the principles and concepts of the present invention and generally designated by the reference numeral 10 will be described.

As best illustrated in FIGS. 1 through 3, the back massaging device 10 generally comprises a body member 12 being designed for being coupled to the wall. The body member 12 can be mounted using screws, glue, double sided tape, suction cups or other means of coupling the body member 12 to the wall. The body member 12 has a length of about 15 inches, a width of about 4 inches and a thickness between about 1 inch and about 2 inches.

A plurality of massaging members 14 are coupled to the body member 12 whereby the massaging members 14 are designed for being positioned opposite the wall when the body member 12 is coupled to the wall. The massaging members 14 are designed for kneading the back of the user when the back of the user is rubbed against the body member 12 and the massaging members 14.

The body member 12 comprises a first portion 16 and a second portion 18. The first portion 16 is coupled to the second portion 18 whereby the first portion 16 is positioned at an angle to the second portion 18. The body portion is positioned around a corner formed by a pair of walls of the structure whereby the first portion 16 is coupled to one of the walls and the second portion 18 is coupled to the other one of the walls to allow the massaging members 14 to be pressed into the back of the user. The body member 12 comprises a flexible material. The flexible material is for permitting the body member 12 to flex whereby the body member 12 is designed for conforming to the angle formed between the walls of the structure. The flexible material of the body member 12 can be transparent or colored to match the color of the wall to provide the least obtrusive appearance when the body member 12 is coupled to the wall.

The body member 12 comprises an exterior surface 20 and an interior surface 22. The interior surface 22 is positioned opposite the exterior surface 20. The interior surface 22 of the body member 12 is designed for being coupled to the wall of the structure. Each the massaging members 14 is coupled to the exterior surface 20 whereby the massaging members 14 extend outwardly from the body member 12.

The body member 12 comprises a pair of side edges 24. One of the side edges 24 is positioned opposite the other one of the side edges 24 of the body member 12. The body member 12 tapers outwardly to the side edges 24 to provide a smoother junction with the wall when the body member 12 is coupled to the wall.

Each of the massaging members 14 comprises a bulbous portion 26 and a base portion 28. The bulbous portion 26 is coupled to the base portion 28. The base portion 28 is coupled to the body member 12 whereby the bulbous portion 26 is positioned opposite the body member 12. The bulbous portion 26 is designed for engaging the back of the user to massage the back of the user.

The massaging members 14 comprise a resiliently flexible material. The resiliently flexible material is designed for permitting the bulbous portion 26 of the massaging members 14 to flex with respect to the base portion 28 of the associated one of the massaging members 14 to conform to the back of the user and massage a greater area of the back of the user. The resiliently flexible material of the massaging members 14 can be transparent or colored to match the color of the wall to provide the least obtrusive appearance when the body member 12 is coupled to the wall.

Each of the massaging members 14 is positioned in a spaced relationship to adjacently positioned massaging members 14. The massaging members 14 is designed for permitting portions of the back of the user to be inserted between the massaging members 14 to allow the massaging members 14 to engaging a greater portion of the back of the user.

In use, the user mounts the body member 12 to the walls so that the body member 12 extends around of corner formed by the two walls. The user can then press their back against the massaging members 14 extending outwardly from the body member 12. The user then rubs their back against the massaging members 14 to massage the back of the user and provide comfort.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A back massaging device for being coupled to a wall of a structure to be rubbed against a back of a user to massage the back of the user, the back massaging device comprising:

a body member being adapted for being coupled to the wall;

a plurality of massaging members being coupled to said body member such that said massaging members are adapted for being positioned opposite the wall when said body member is coupled to the wall, said massaging members being adapted for kneading the back of the user when the back of the user is rubbed against said body member and said massaging members;

said body member comprising a first portion and a second portion, said first portion being coupled to said second portion such that said first portion is positioned at an angle to said second portion, said body portion being positioned around a corner formed by a pair of walls of the structure such that said first portion is coupled to one of the walls and said second portion is coupled to the other one of the walls to allow the massaging members to be pressed into the back of the user;

said body member comprising a flexible material, said flexible material being for permitting said body member to flex such that said body member is adapted for conforming to the angle formed between the walls of the structure;

said body member comprising an exterior surface and an interior surface, said interior surface being positioned opposite said exterior surface, said interior surface of said body member being adapted for being coupled to the wall of the structure, each said massaging members being coupled to said exterior surface such that said massaging members extend outwardly from said body member;

said body member comprising a pair of side edges, one of said side edges being positioned opposite the other one of said side edges of said body member, said body member tapering outwardly to said side edges to provide a smoother junction with the wall when said body member is coupled to the wall;

each of said massaging members comprising a bulbous portion and a base portion, said base portion having a proximal end and a distal end, said bulbous portion being coupled to the distal end of said base portion, the proximal end of said base portion being coupled to said body member such that said bulbous portion is positioned opposite said body member, said bulbous portion being adapted for engaging the back of the user to massage the back of the user;

each of said base portions of said massaging members having a width, the width of each of said base portions tapering thinner toward a middle section of said base portions and the width of each of said base portions expanding wider toward said proximal and distal ends to form a necked profile at the middle section of said base portions;

said massaging members comprising a resiliently flexible material, said resiliently flexible material being adapted for permitting said bulbous portion of said massaging members to flex with respect to said base portion of the associated one of said massaging members to conform to the back of the user and massage a greater area of the back of the user; and each of said massaging members being positioned in a spaced relationship to adjacently positioned massaging members, said massaging members being adapted for permitting portions of the back of the user to be inserted between said massaging members to allow the massaging members to engaging a greater portion of the back of the user;

each of said bulbous portions of said massaging members having a width, said bulbous portions of adjacent said massaging members being spaced from each other a distance substantially equal to the width of said bulbous portions.

* * * * *